United States Patent [19]
Kent et al.

[11] Patent Number: 6,057,459
[45] Date of Patent: May 2, 2000

[54] PREPARATION OF CARBOCYCLIC COMPOUNDS

[75] Inventors: Kenneth M. Kent, Sunnyvale; Choung U. Kim, San Carlos; Lawrence R. McGee, Pacifica; John D. Munger, Jr., Alviso; Ernest J. Prisbe, Los Altos; Michael J. Postich, San Mateo; John C. Rohloff, Mountain View; Daphne E. St. John, San Francisco; Matthew A. Williams; Lijun Zhang, both of Foster City, all of Calif.

[73] Assignee: Gilead Sciences, Inc., Foster City, Calif.

[21] Appl. No.: 09/175,744

[22] Filed: Oct. 20, 1998

Related U.S. Application Data

[62] Division of application No. 08/701,942, Aug. 23, 1996, Pat. No. 5,859,284.

[51] Int. Cl.$^7$ .................................................. C07D 317/68
[52] U.S. Cl. ........................................................ 549/436
[58] Field of Search ............................................ 549/436

[56] References Cited

U.S. PATENT DOCUMENTS

| | | | |
|---|---|---|---|
| 4,968,788 | 11/1990 | Farquhar ..................................... | 536/27 |
| 5,175,273 | 12/1992 | Bischofberger et al. . | |
| 5,206,400 | 4/1993 | Witiak et al. . | |
| 5,292,938 | 3/1994 | Mease et al. . | |
| 5,360,817 | 11/1994 | von Izstein et al. ..................... | 514/459 |
| 5,428,073 | 6/1995 | Kunisch et al. . | |
| 5,512,596 | 4/1996 | Kim et al. ............................... | 514/568 |
| 5,514,798 | 5/1996 | Bischofberger et al. . | |
| 5,536,734 | 7/1996 | Mueller et al. ......................... | 514/336 |
| 5,556,963 | 9/1996 | Liav et al. . | |
| 5,597,933 | 1/1997 | Searle et al. . | |
| 5,602,277 | 2/1997 | Babu et al. . | |
| 5,622,916 | 4/1997 | Kunisch et al. . | |
| 5,714,509 | 2/1998 | Luo et al. . | |
| 5,763,483 | 6/1998 | Bischofberger et al. ................ | 514/529 |
| 5,866,601 | 2/1999 | Lew et al. ............................... | 514/459 |
| 5,886,213 | 3/1999 | Kent et al. ............................... | 560/156 |
| 5,952,375 | 9/1999 | Bischofberger et al. ................ | 514/459 |

FOREIGN PATENT DOCUMENTS

| | | |
|---|---|---|
| 77590 | 11/1991 | Australia . |
| PK 2896 | 11/1991 | Australia . |
| 654815 | 11/1994 | Australia . |
| 0 534 216 A1 | 9/1992 | European Pat. Off. . |
| 0 539 204 A1 | 10/1992 | European Pat. Off. . |
| 9510141 | 5/1995 | United Kingdom . |
| 9516276 | 8/1995 | United Kingdom . |
| 9525389 | 12/1995 | United Kingdom . |
| WO 91/16320 | 10/1991 | WIPO . |
| WO 92/06691 | 4/1992 | WIPO . |
| WO 93/12105 | 6/1993 | WIPO . |
| WO 93/16049 | 8/1993 | WIPO . |
| WO 94/07885 | 4/1994 | WIPO . |
| WO 94/07886 | 4/1994 | WIPO . |
| WO 94/28956 | 12/1994 | WIPO . |
| WO 94/29476 | 12/1994 | WIPO . |
| WO 95/00503 | 1/1995 | WIPO . |
| WO 95/16680 | 6/1995 | WIPO . |
| WO 95/18800 | 7/1995 | WIPO . |
| WO 95/20583 | 8/1995 | WIPO . |
| WO 95/32712 | 12/1995 | WIPO . |
| WO 96/04265 | 2/1996 | WIPO . |
| WO 96/26933 | 9/1996 | WIPO . |
| WO 96/30329 | 10/1996 | WIPO . |
| WO 96/34603 | 11/1996 | WIPO . |
| WO 96/36628 | 11/1996 | WIPO . |
| WO 96/39838 | 12/1996 | WIPO . |

OTHER PUBLICATIONS

Ulibarri et al., J. Org. Chem., May 5, 1995, vol. 60, No. 9, pp. 2753–2761, May 1995.

Bamford et al., "Synthesis of 6–, 7– and 8–carbon sugar analogues of potent anti–influenza 2,3–didehydro–2,3–dideoxy–N–acetylneuraminic acid derivatives", pp. 1181–1187, J Chem Soc Perkin Trans I, 1995.

Bamford, Mark J., "Neuraminidase Inhibitors as Potential Anti–Influenza Drugs", 10:1–16, J Enzyme Inhibition, 1995.

Burger, Alfred, "Relation of Chemical Structure and Biological Activity", Third edition, part 1, pp. 73–75, Medicinal Chemistry, 1979.

Carless et al., "Synthesis of Pseudo–alpha–L–fucopyranose from Toluene", pp. 2447–2448, J Chem Soc (C), 1995.

Chahoua et al., "Synthesis of (–)–Shikimate and (–)–Quinate 3–Phosphates by Differentiation of the Hydroxyl Functions of (–)–Shikimic and (–)–Quinic Acids", 57:5798–5801 J Org Chem, 1992.

Chandler et al., "Synthesis of the potent influenza neuraminidase inhibitor 4–guanidino Neu5Ac2en. X–Ray molecular structure of 5–acetamido–4–amino–2,6–anhydro–3,4,5–trideoxy–D–erythro–L–gluco–nononic acid", pp. 1173–1180, J Chem Soc Perkin Trans I, 1995.

Chandler et al., "Approaches to carbocyclic analogues of the potent neuraminidase inhibitor 4–guanidino–Neu5Ac2en. X–Ray molecular structure of N–[(S,2S, 6R)–2–azido–6–benzyloxymethyl–4–formylcyclohex–3–enyl]acetamide", pp. 1189–1197, J Chem Soc Perkin Trans I, 1995.

Ciccotosto et al., "Synthesis of Methyl 5–Acetamido–3,4,5–trideoxy–4–Guanidinyl–D–glycero–D–galacto–2–nonulopyranosidonic acid (4–deoxy–4–guanidino– Neu5Acalpha2Me)", 36(30):5405–5408, Tet Lett, 1995.

Colman, P.M., "Influenza virus neuraminidase: Structure, antibodies, and inhibitors", 3:1687–1696, Protein Science, 1994.

Dernick, Rudolf, "Sterical Requirements for Inhibitors of Viral Neuraminidases", 96:256, Chem Ab, 1982.

(List continued on next page.)

Primary Examiner—Laura L. Stockton
Attorney, Agent, or Firm—Mark L. Bosse

[57] ABSTRACT

The present invention provides new synthetic methods and compositions. In particular, new methods of preparing intermediates useful in the synthesis of neuraminidase inhibitors and compositions useful as intermediates that are themselves useful in the synthesis of neuraminidase inhibitors are provided.

1 Claim, No Drawings

OTHER PUBLICATIONS

Douglas, R. Gordon, Jr., "Prophylaxis and Treatment of Influenza", 322(7):443–450, N Engl J Med, Feb. 15, 1990.

Fernandez et al., "New and Efficient Enantiospecific Synthesis of (–)–Methyl 5–epi–Shikimate and Methyl 5–epi–Quinate from (–)–Quinic Acid", 38(29):5225–5228, Tet Lett, 1997.

Funded Research Agreement, "Agreement between Gilead Sciences, Inc. and the University of California, Berkeley", 2 pages,, Dec. 7, 1995.

Ganem, Bruce, "Tetrahedron Report Number 59. From Glucose to Aromatics: Recent Developments in Natural Products of the Shikimic Acid Pathway", 34:3353–3383, Tetrahedron, 1978.

Grewe et al, "Eine einfache Synthese der Shikimisaure", 100:2546–2553, Chem Ber, 1967.

Grewe et al, "Synthese der Homochinasaure und des beta–Chino–athylamins", 575:1–17, Liebigs Ann Chem, 1952.

Grewe et al, "Darstellung und Eigenschaften des Chinaaldehyds", 658:113–119, Liebigs Ann Chem, 1962.

Grewe et al, "Uberfuhrung der Chinasaure in ungesattigte Verbindungen vom Typ der Shikimisaure", Angew Chem Int Ed, 1957.

Grewe et al, "Die Uberfuhrung der Shikimisaure in Chinasaure", 86:928–938, Chem Ber, 1953.

Grewe et al, "Die Totalsynthese der Chinasaure", 87:793–802, Chem Ber, 1954.

Grewe et al, "Eine neue Synthese der Shikimisaure", 97:443–448, Chem Ber, 1964.

Grewe et al, "Abbau der Chinasaure nach Hunsdiecker", 98:104–110, Chem Ber, 1965.

Hanessian et al., "Anomeric Deoxygenation of 2–Ulosonic Acids Using SmI2: Rapid Access to 2–Deoxy–KDO and 2–Deoxy–NANA", pp. 863–864, Synlett, Oct. 1994.

Hayden et al., "Safety and Efficacy of the Neuraminidase Inhibitor GG167 in Experimental Human Influenza", 275(4):295–299, JAMA, Jan. 1996.

Janakiraman et al., "Structure of Influenza Virus Neuraminidase B/Lee/40 Complexed with Sialic Acid and a Dehydro Analog at 1.8–Angstrom Resolution: Implications for the Catalytic Mechanism", 33:8172–8179, Biochem, 1994.

Kiefel et al., "Synthesis and Biological Evaluation of N–Acetylneuraminic Acid–Based Rotavirus Inhibitors", 39:1314–1320, J Med Chem, 1996.

Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti–Influenza Activity", 119:681–690, J Am Chem Soc, 1997.

Kong et al., "The First Synthesis of a C–7 Nitrogen–containing Sialic Acid Analogue, 5–Acetamido–7–azido–3,5, 7–trideoxy–D–glycero–D–galacto–2–nonulopyranosonic acid (7–azido–7–deoxy–Neu5Ac)", 36(6):957–960, Tet Lett, 1995.

Kudo et al., "Synthesis of the Potent Inhibitors of Neuraminidase, N–(1,2–Dihydroxypropyl) Derivatives of Siastatin B and its 4–Deoxy Analogs", 46(2):300–309, J Antibiot, Feb. 1993.

Luo et al., "Abstract of Presentation C52: Designed Non-–Carbohydrate Inhibitors or Influenza Virus Neuraminidase and Accompanying Notes", International Antiviral Conference, Nice, France, Jun. 10, 1994.

McCauley et al., "4–Guanidino–Neu5Ac2en fails to protect chickens from infection with highly pathogenic avian influenza virus", 27:179–186, Antiviral Res, 1995.

McKimm–Breschkin et al., "Generation and Characterization of Variants of NWS/G70C Influenza Virus after In Vitro Passage in 4–Amino–Neu5Ac2en and 4–Guanidino–Neu5Ac2en", 40(1):40–46, Antimicro Ag & Chemo, Jan. 1996.

Meindl et al., "2–Deoxy–2,3–dehydrosialic acids. 3. Inhibition of Vibrio cholerae[comma]neuraminidase by oxidation products of 2–deoxy–2,3–dehydro–N–acetylneuraminic acid", 73:42027b, Chem Ab, 1970.

Nishimura et al., "Design of Potential Neuraminidase Inhibitors By Dehydration, Deoxygenation and Epimerization of Siastatin B", 1(1):39–44, Natural Product Letters, 1992.

Nishimura et al., "Synthesis of 3–Episiastatin B Analogues Having Anti–Influenza Virus Activity", 46(12):1883–1889, J Antibiot, Dec. 1993.

Ogawa et al., "Synthesis of carbocyclic analogues of 3–deoxy–D–manno–2–octulosonic acid and N–acetylneuraminic acid", 269:53–78, Carb Res, 1995.

Ogawa et al., "Synthesis of a Carbocyclic Analogue of N–Acetylneuraminic Acid (Pseudo–N–acetylneuraminic Acid)", pp. 406–408, J Chem Soc (C), 1992.

Raner et al., 43:609–616, Aust J Chem, 1990.

Ryan et al., "Inhibition of Influenza Virus Replication in Mice by GG167 (4–Guanidino–2,4–Dideoxy–2,3–Dehydro–N–Acetylneuraminic Acid) Is Consistent with Extracellular Activity of Viral Neuraminidase (Sialidase)", 38(10):2270–2275, Antimicro Ag & Chemo, Oct. 1994.

Saito et al., "Steps in Maturation of Influenza A Virus Neuraminidase", 69(8):5011–5017, J Virol, Aug. 1995.

Singh et al., "Structure–Based Inhibitors of Influenza Virus Sialidase. A Benzoic Acid Lead with Novel Interaction", 38:3217–3225, J Med Chem, 1995.

Smith et al., "Synthesis and influenza virus sialidase inhibitory activity of analogues of 4–guanidino–Neu5Ac2en (GG167) with modified 5–substituents", 31:143–150, Eur J Med Chem, Jun. 22, 1995.

Smith et al., "Novel Inhibitors of Influenza Sialidases Related to GG167", 6(24):2931–2936, Bioorg Med Chem Lett, 1996.

Sollis et al, "Novel Inhibitors of Influenza Sialidase Related to GG167", 6(15):1805–1808, Abstract, Table of Contents, Bioorg Med Chem Lett, 1996.

Starkey et al., "Synthesis and Influenza Virus Sialidase Inhibitory Activity of the 5–Desacetamido Analogue of 2,3–Didehydro–2, 4–dideoxy–4–guanidinyl–N–acetylneuraminic acid", 36(2):299–302, Tet Lett, 1995.

Staschke et al., "Molecular Basis for the Resistance of Influenza Viruses to 4–Guanidino–Neu5Ac2en", 214:642–646, Virology, 1995.

Stevens, Ray, "Letter from Assistant Prof. Ray Stevens to Dr. Choung Kim", 1 page, Oct. 10, 1996.

Stevens, Ray, "Letter from Assistant Prof. Ray Stevens to Dr. Choung Kim", 2 pages,, Feb. 18, 1996.

Ulibarri et al., "Construction of the Bicyclic Core Structure of the Enediyne Antibiotic Esperamicin–A1 in Either Enantiomeric Form from (–)–Quinic Acid", 60:2753–2761, J Org Chem, 1995.

Ulmer et al., "Heterologous Protection Against Influenza by Injection of DNA Encoding a Viral Protein", 259:1745–1749, Science, Mar. 19, 1993.

Wu et al., "Non–Sialate Inhibitor of Influenza A/WSN/33 Neuraminidase", 34:7154–7160, Biochem, 1995.

von Itzstein et al, "Rational design of potent sialidase–based inhibitors of influenza virus replication", 363:418–423, Nature, 1993.

von Itzstein et al., "A Study of the Active Site of Influenza Virus Sialidase: An Approach to the Rational Design of Novel Anti–influenza Drugs", 39:388–391, J Med Chem, 1996.

PREPARATION OF CARBOCYCLIC COMPOUNDS

This application is a divisional of U.S. Ser. No. 08/701,942 filed Aug. 23, 1996 now U.S. Pat. No. 5,859,284, which is incorporated herein by reference.

FIELD OF THE INVENTION

The present invention is directed to methods of preparing carbocyclic compounds and intermediates therefore.

BRIEF DESCRIPTION OF RELATED ART

United States Patent Application (having Attorney Docket No. 205.6) Serial Number (not yet known), filed Aug. 23, 1996, which was a continuation-in-part application of U.S. patent application Ser. No. 08/653,034, filed Mar. 24, 1996, which was a continuation-in-part application of U.S. patent application Ser. No. 08/606,624, filed Feb. 26, 1996, which was a continuation-in-part application of U.S. patent application Ser. No. 08/580,567, filed Dec. 29, 1995, which was a continuation-in-part application of U.S. patent application Ser. No. 08/476,946, filed Jun. 6, 1995, which was a continuation-in-part application of U.S. patent application Ser. No. 08/395,245, filed Feb. 27, 1995, all of which are incorporated herein by reference in their entirety, describe, inter alia, neuraminadase inhibitors and intermediates in the synthesis of neuraminidase inhibitor. The present invention provides processes useful in the preparation of these compositions.

OBJECTS OF THE INVENTION

Selected embodiments of the invention are directed to one or more of the following objects:

A principal object of the invention is to provide new synthetic methods and compositions.

An additional object of the invention is to provide new methods of preparing intermediates useful in the synthesis of neuraminidase inhibitors.

An additional object of the invention is to provide compositions useful as intermediates that are themselves useful in the synthesis of neuraminidase inhibitors.

An additional object of the invention is to provide compositions useful as neuraminidase inhibitors.

SUMMARY OF THE INVENTION

One aspect of the present invention is directed to processes for the preparation of compounds of the formula:

5 wherein:
$R^1$ is a cyclic hydroxy protecting group;
$R^2$ is a carboxylic acid protecting group;
$R^3$ is a hydroxy protecting group; and
each $R^{20}$ is independently H or an alkyl of 1 to 12 carbon atoms; which process comprises reaction of a compound of the formula:

4 with a dehydrating reagent.

Another aspect of the present invention is directed to processes for the preparation of compounds of the formula:

11 wherein:
each of $R^2$, $R^3$ and $R^{20}$ are as defined above;
$R^4$ is $—C(R^{30})_3$;
each $R^5$ is independently H or $R^3$;
each $R^7$ is independently H or an amino protecting group;
each $R^8$ is independently H or $R^2$;
each $R^9$ is independently H or a thiol protecting group;
each $R^{21}$ is independently $R^{20}$, Br, Cl, F, I, CN, $NO_2$ or $N_3$;
each $R^{22}$ is independently F, Cl, Br, I, —CN, $N_3$, $—NO_2$, $—OR^5$, $—OR^{20}$, $—N(R^{20})_2$, $—N(R^{20})(R^7)$, $—N(R^7)_2$, $—SR^{20}$, $—SR^9$, $—S(O)R^{20}$, $—S(O)_2R^{20}$, $—S(O)OR^{20}$, $—S(O)OR^8$, $—S(O)_2OR^{20}$, $—S(O)_2OR^8$, $—C(O)OR^{20}$, $—C(O)OR^8$, $—OC(O)R^{20}$, $—N(R^{20})(C(O)R^{20})$, $—N(R^7)(C(O)R^{20})$, $—N(R^{20})(C(O)OR^{20})$, $—N(R^7)(C(O)OR^{20})$, $—C(O)N(R^{20})_2$, $—C(O)N(R^7)(R^{20})$, $—C(O)N(R^7)_2$, $—C(NR^{20})(N(R^{20})_2)$, $—C(N(R^7))(N(R^{20})_2)_2$, $—C(N(R^{20}))(N(R^{20})(R^7))$, $—C(N(R^7))(N(R^{20})(R^7))$, $—C(N(R^{20}))(N(R^7)_2)$, $—C(N(R^7))(N(R^7)_2)$, $—N(R^{20})C(N(R^{20}))(N(R^{20})_2)$, $—N(R^{20})C(N(R^{20}))(N(R^{20})(R^7))$, $—N(R^{20})C(N(R^7))(N(R^{20})_2)$, $—N(R^7)C(N(R^{20}))(N(R^{20})_2)$, $—N(R^7)C(N(R^7))(N(R^{20})_2)$, $—N(R^7)C(N(R^{20}))(N(R^{20})(R^7))$, $—N(R^{20})C(N(R^7))(N(R^7)_2)$, $—N(R^7)C(N(R^{20}))(N(R^7)_2)$, $—N(R^{20})C(N(R^{20}))(N(R^7)_2)$, $—N(R^{20})C(N(R^7))(N(R^7)_2)$, $—N(R^7)C(N(R^7))(N(R^7)_2)$, $=O$, $=S$, $=N(R^{20})$, $=N(R^7)$ or W;
each $R^{23}$ is independently alkyl of 1 to 11 carbon atoms, alkenyl of 2 to 11 carbon atoms, or alkynyl of 2 to 11 carbon atoms;
each $R^{24}$ is independently $R^{23}$ wherein each $R^{23}$ is substituted with 0 to 3 $R^{22}$ groups;
each $R^{24a}$ is independently alkylene of 1 to 11 carbon atoms, alkenylene of 2 to 11 carbon atoms, or alkynylene of 2–11 carbon atoms any one of which alkylene, alkenylene or alkynylene is substituted with 0–3 $R^{22}$ groups; compound;
each $R^{28}$ is independently alkyl of 1 to 12 carbon atoms, alkenyl of 2 to 12 carbon atoms, or alkynyl of 2 to 12 carbon atoms;
each $R^{29}$ is independently $R^{22}$ or $R^{28}$ wherein each $R^{28}$ is substituted with 0 to 3 $R^{22}$ groups;

each $R^{30}$ is independently H, $R^{24}$, W or —$R^{24a}$W; and
each W is independently carbocycle or heterocycle wherein any one of which carbocycle or heterocycle is substituted with 0 to 3 $R^{29}$ groups;
which process comprises reaction of a compound of the formula:

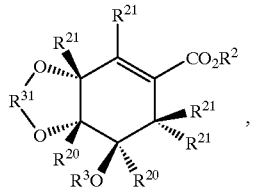

wherein $R^{31}$ is a ketal or acetal, with a lewis acid reagent; provided that $R^4$, taken as a whole, contains:
   0 to 3 W groups substituted with 0 to 3 $R^{29}$ groups; and, in addition, 1 to 12 carbon atoms substituted with 0 to 3 $R^{22}$ groups.

Another aspect of the present invention is directed to processes for the preparation of compounds of the formula:

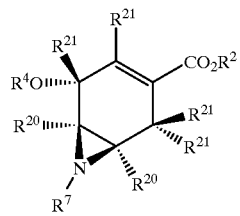

wherein:
   $R^2$, $R^4$, $R^7$, $R^{20}$ and $R^{21}$ are as defined above. which process comprises reaction of a compound of the formula:

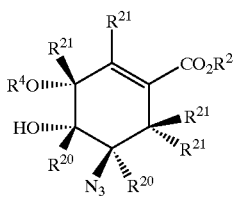

with a reducing reagent.

Another aspect of the present invention is directed to processes for the preparation of compounds of the formula:

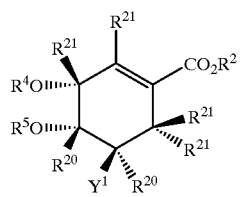

wherein:
   $R^2$, $R^4$, $R^5$, $R^{20}$ and $R^{21}$ are as described above; and
   $Y^1$ is a mono-, di- or unsubstituted amino group; which process comprises reaction of a compound of the formula:

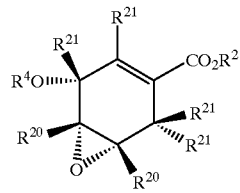

with an amine reagent.

Another aspect of the present invention is directed to processes for the preparation of compounds of the formula:

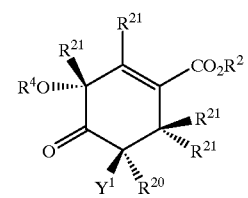

wherein:

$R^2$, $R^4$, $R^{20}$, $R^{21}$ and $Y^1$ are as described above;

which process comprises reaction of a compound of the formula:

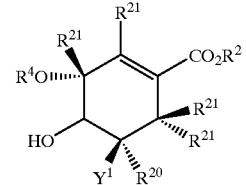

with an oxidizing reagent.

Another aspect of the present invention is directed to processes for the preparation of compounds of the formula:

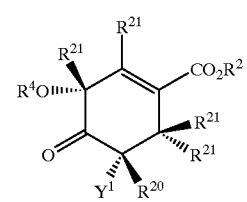

wherein:

$R^2$, $R^4$, $R^{20}$, $R^{21}$ and $Y^1$ are as described above; which process comprises reaction of a compound of the formula:

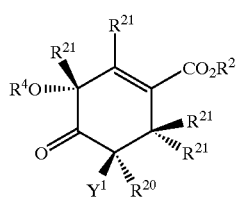

with a base.

Another aspect of the present invention is directed to processes for the preparation of compounds of the formula:

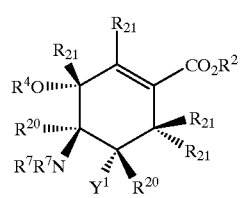

wherein:

$R^2$, $R^4$, $R^7$, $R^{20}$, $R^{21}$ and $Y^1$ are as described above; which process comprises reaction of a compound of the formula:

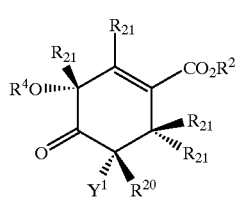

with a reductive amination reagent.

DETAILED DESCRIPTION

General

The present invention is directed to methods of making the compositions described herein. Even though the compositions of the invention are prepared by any of the applicable techniques of organic synthesis, the present invention provides advantageous methods for accomplishing the preparations.

Many conventional techniques are well known in the art and will not be elaborated here. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in—Chief (Pergamon Press, New York, 1993 printing).

Generally, the reaction conditions such as temperature, reaction time, solvents, workup procedures, and the like, will be those common in the art for the particular reaction to be performed. The cited reference material, together with material cited therein, contains detailed descriptions of such conditions.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.1 M to 10 M, typically 0.1 M to 1 M), temperatures (−100° C. to 250° C., typically −78° C. to 150° C., more typically −78° C. to 100° C., still more typically 0° C. to 100° C.), solvents (aprotic or protic), reaction times (typically 10 seconds to 10 days, more typically 1 min. to 10 hours, still more typically 10 min. to 6 hours), reaction vessels (typically glass, plastic, metal), pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic sysnthesis selects conditions and apparatus reasonably expected to successfully carry out the chemical reactions of the described processes based on the knowledge in the art.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable. Workup typically consists of quenching any unreacted reagents followed by partition between a water/organic layer system (extraction) and separating the layer containing the product. Each of the products of the following processes is optionally separated, isolated, and/or purified prior to its use in subsecquent processes.

Embodiments

One aspect of the present invention is directed to processes for the preparation of compounds of the formula:

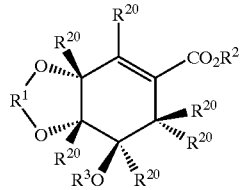

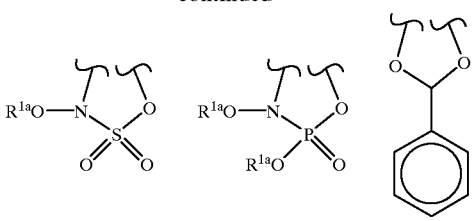

$R^1$ is a cyclic hydroxy protecting group. A very large number of common protecting groups (including cyclic hydroxy protecting groups) and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994). In particular Chapter 1, Protecting Groups: An Overview, pages 1–20, Chapter 2, Hydroxyl Protecting Groups, pages 21–94, Chapter 3, Diol Protecting Groups, pages 95–117, Chapter 4, Carboxyl Protecting Groups, pages 118–154, Chapter 5, Carbonyl Protecting Groups, pages 155–184, and Chapter 6, Amino Protecting Groups, pages 185–243. Typically, the cyclic hydroxyprotecting groups are those commonly useful as 1,2-diol protecting groups.

Typical 1,2-diol protecting groups (thus, generally where two OH groups are taken together with the RI protecting functionality) are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table A, or ayalic ketals or acetals. Still more typically, cyclic ketals and acetals.

Table A

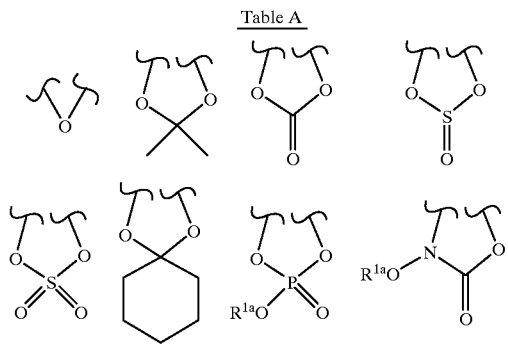

wherein $R^{1a}$ is $C_1$–$C_6$ alkyl (as defined immediately below).

"Alkyl" as used herein, unless stated to the contrary, is $C_1$–$C_6$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$). Typical alkyls are methyl, ethyl, 1-propyl, and 2-propyl.

$R^2$ is a carboxylic acid protecting group. Typical carboxylic acid protecting groups are $R^{25}$ (described immediately below) or those described in Greene at pages 224–276. Those described in Greene include Esters (Methyl); Substituted Methyl Esters (9-Fluorenylmethyl, Methoxymethyl, Methylthiomethyl, Tetrahydropyranyl, Tetrahydrofuranyl, Methoxyethoxymethyl, 2-(Trimethylsilyl)ethoxymethyl, Benzyloxymethyl, Phenacyl, p-Bromophenacyl, α-Methylphenacyl, p-Methoxyphenacyl, Carboxamidomethyl, N-Phthalimidomethyl); 2-Substituted Ethyl Esters (2,2,2-Trichloroethyl, 2-Haloethyl, ω-Chloroalkyl, 2-(Trimethylsilyl)ethyl, 2-Methylthioethyl, 1,3-Dithianyl-2-methyl, 2-(p-Nitrophenylsulfenyl)ethyl, 2-(p-Toluenesulfonyl)ethyl, 2-(2'-Pyridyl)ethyl, 2-(Diphenylphosphino)ethyl, 1-Methyl-1-phenylethyl, t-Butyl, Cyclopentyl, Cyclohexyl, Allyl, 3-Buten-1-yl, 4-(Trimethylsilyl)-2-buten-1-yl, Cinnamyl, α-Methylcinnamyl, Phenyl, p-(Methylmercapto)phenyl, Benzyl); Substituted Benzyl Esters (Triphenylmethyl, Diphenylmethyl, Bis(o-nitrophenyl)methyl, 9-Anthrylmethyl, 2-(9,10-Dioxo)anthrylmethyl, 5-Dibenzosuberyl, 1-Pyrenylmethyl, 2-(Trifluoromethyl)-6-chromylmethyl, 2,4,6-Trimethylbenzyl, p-Bromobenzyl, o-Nitrobenzyl, p-Nitrobenzyl, p-Methoxybenzyl, 2,6-Dimethoxybenzyl, 4-(Methylsulfinyl)benzyl, 4-Sulfobenzyl, Piperonyl, 4-Picolyl, p-poly-Benzyl); Silyl Esters (Trimethylsilyl, Triethylsilyl, t-Butyldimethylsilyl, i-Propyldimethylsilyl, Phenyldimethylsilyl, Di-t-butylmethylsilyl); Activated Esters (Thiols); Miscellaneous Derivatives (Oxazoles, 2-Alkyl-1,3-oxazolines, 4-Alkyl-5-oxo-1,3-oxazolidines, 5-Alkyl-4-oxo-1,3-dioxolanes, Ortho Esters, Phenyl Group, Pentaaminocobalt(III) Complex);

Stannyl Esters (Triethylstannyl, Tri-n-butylstannyl); Amides (N,N-Dimethyl, Pyrrolidinyl, Piperidinyl, 5,6-Dihydrophenanthridinyl, o-Nitroanilides, N-7-Nitroindolyl, N-8-Nitro-1,2,3,4-tetrahydroquinolyl, p-poly-Benzenesulfonamides); and Hydrazides (Hydrazides, N-Phenyl, N,N'-Diisopropyl).

$R^{25}$ is alkyl of 1 to 12 carbon atoms, alkenyl of 2 to 12 carbon atoms, or alkynyl of 2 to 12 carbon atoms, any one of which alkyl, alkenyl, or alkynyl is substituted with 0–3 $R^{22}$ groups ($R^{22}$ is described below). More typically $R^{25}$ is alkyl of 1 to 6 carbon atoms, alkenyl of 2 to 6 carbon atoms, or alkynyl of 2 to 6 carbon atoms, any one of which alkyl, alkenyl, or alkynyl is substituted with 0–3 $R^{22}$ groups. Still more typically, $R^{25}$ is alkyl of 1 to 8 carbon atoms substituted with 0–2 $R^{22}$ groups. Even more typically, $R^{25}$ is alkyl of 1, 2, 3, 4, 5, 6, 7, or 8 carbon atoms. Most typically $R^{25}$ is methyl, ethyl, 1-propyl or 2-propyl.

"Alkenyl" as used herein, unless stated to the contrary, is $C_1$–$C_6$ hydrocarbon containing normal, secondary, tertiary or cyclic carbon atoms. Examples are ethenyl (—CH=CH$_2$), 1-prop-1-enyl (—CH=CHCH$_3$), 1-prop-2-enyl (—CH$_2$CH=CH$_2$), 2-prop-1-enyl (—C(=CH$_2$)(CH$_3$)), 1-but-1-enyl (—CH=CHCH$_2$CH$_3$), 1-but-2-enyl (—CH$_2$CH=CHCH$_3$), 1-but-3-enyl (—CH$_2$CH$_2$CH=CH$_2$), 2-methyl-1-prop-1-enyl (—CH=C(CH$_3$)$_2$), 2-methyl-1-prop-2-enyl (—CH$_2$C(=CH$_2$)(CH$_3$)), 2-but-1-enyl (—C(=CH$_2$)CH$_2$CH$_3$), 2-but-2-enyl (—C(CH$_3$)=CHCH$_3$), 2-but-3-enyl (—CH(CH$_3$)CH=CH$_2$), 1-pent-1-enyl (—C=CHCH$_2$CH$_2$CH$_3$), 1-pent-2-enyl (—CHCH=CHCH$_2$CH$_3$), 1-pent-3-enyl (—CHCH$_2$CH=CHCH$_3$), 1-pent-4-enyl (—CHCH$_2$CH$_2$CH=CH$_2$), 2-pent-1-enyl (—C(=CH$_2$)CH$_2$CH$_2$CH$_3$), 2-pent-2-enyl (—C(CH$_3$)=CH$_2$CH$_2$CH$_3$), 2-pent-3-enyl (—CH(CH$_3$)CH=CHCH$_3$), 2-pent-4-enyl (—CH(CH$_3$)CH$_2$CH=CH$_2$) or 3-methyl-1-but-2-enyl (—CH$_2$CH=C(CH$_3$)$_2$). More typically, alkenyl groups are of 2, 3 or 4 carbon atoms.

"Alkynyl" as used herein, unless stated to the contrary, is $C_1$–$C_6$ hydrocarbon containing normal, secondary, tertiary or cyclic carbon atoms. Examples are ethynyl (—C≡CH), 1-prop-1-ynyl (—C≡CCH$_3$), 1-prop-2-ynyl (—CH$_2$C≡CH), 1-but-1-ynyl (—C≡CCH$_2$CH$_3$), 1-but-2-ynyl (—CH$_2$C≡CCH$_3$), 1-but-3-ynyl (—CH$_2$CH$_2$C≡CH), 2-but-3-ynyl (CH(CH$_3$)C≡CH), 1-pent-1-ynyl (—C≡CCH$_2$CH$_2$CH$_3$), 1-pent-2-ynyl (—CH$_2$C≡CCH$_2$CH$_3$), 1-pent-3-ynyl (—CH$_2$CH$_2$C≡CCH$_3$) or 1-pent-4-ynyl (—CH$_2$CH$_2$CH$_2$C≡CH). More typically, alkynyl groups are of 2, 3 or 4 carbon atoms.

$R^3$ is a hydroxy protecting group. Typical $R^3$ hydroxy protecting groups described in Greene (pages 14–118) include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, $R^3$ hydroxy protecting groups include substituted methyl ethers, substituted benzyl ethers, silyl ethers, and esters including sulfonic acid esters, still more typically, trialkylsilyl ethers, tosylates, mesylates and acetates.

Each $R^{20}$ is independently H or an alkyl of 1 to 12 carbon atoms. Typically $R^{20}$ is H or alkyl of 1 to 6 carbon as described above. Still more typically, $R^{20}$ is H or methyl. More typically yet, $R^{20}$ is H.

This process embodiment comprises reaction of a compound of the formula:

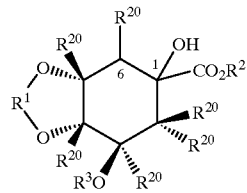

4

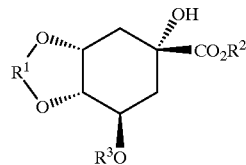

6 with a dehydrating reagent. Typically the hydroxy group at position 1 is eliminated without removing the cis-4,5-diol protecting group. The hydroxy group at position 1 is eliminated to form an olefinic bond between positions 1 and 6.

Typically the process comprises treating compound 4 with a suitable dehydrating agent, such as a mineral acid (HCl, $H_2SO_4$) or $SO_2Cl_2$. More typically, compound 4 is treated with $SO_2Cl_2$, followed by an alkanol. Still more typically, compound 4 is treated with $SO_2Cl_2$ in a suitable polar, aprotic solvent, such as an amine to form an olefin. More typically yet, compound 4 is treated with $SO_2Cl_2$ in pyridine/$CH_2Cl_2$ at a temperature between $-100°$ C. and $0°$ C., typically $-100°$ C. and $-10°$ C., more typically $-78°$ C., to form compound 5.

In a typical embodiment, a solution of compound 4 and pyridine in dichloromethane is cooled to $-20°$ to $-30°$ C. and treated portionwise with sulfuryl chloride. After the exothermic reation subsided, the resulting slurry is quenched with ethanol, warmed to $0°$ C., and washed successively with 16% sulfuric acid, water and 5% aqueous sodium bicarbonate. A detailed example of this embodiment is provided as Example 4 below.

Optionally, the process of this embodiment further comprises purifying or separating compound 5 from any other reaction products or other contaminents such as other double bond isomers, halogenated side products or starting materials and reagents by treatment with a noble metal complex. Noble metals include gold, silver, platinum, palladium, iridium, rhenium, mercury, ruthenium and osmium. Typically, the noble metal complex of this embodiment is a complex of platinum or palladium. More typically the complex is a palladium (0) complex, still more typically, the complex is a tetrakis(triarylphosphine)palladium (0) complex.

In a typical embodiment the organic layer of the reaction contains a mixture of olefin and halogenated products as well as starting material. It is concentrated in vacuo and ethyl acetate is added. The solution is treated with pyrrolidine and tetrakis(triphenylphosphine)palladium(0) at ambient temperature, followed by washing with 16% sulfuric acid. The organic layer is filtered through a pad of silica gel and eluted with ethyl acetate. The filtrate is concentrated in vacuo. The residue is dissolved in ethyl acetate at reflux and hexane is added. Upon cooling, the product crystallizes and is separated by filtration and washed with 14% ethyl acetate in hexane. After drying in vacuo, 5 was obtained. A detailed example of this embodiment is provided as Example 4 below.

In another example of this embodiment compound 5 is of the formula:

Another aspect of the present invention is directed to processes for the preparation of compounds of the formula:

11 wherein:

$R^2$, $R^3$ and $R^{20}$ are as defined above.

$R^4$ is described below.

W is carbocycle or heterocycle wherein any one of which carbocycle or heterocycle is substituted with 0 to 3 $R^{29}$ groups ($R^{29}$ is described below).

W is a carbocycle or heterocycle, with the proviso that each W is independently substituted with 0 to 3 $R^{29}$ groups ($R^{29}$ is described below). W carbocycles and heterocycles are stable chemical structures. Such structures are isolatable in measurable yield, with measurable purity, from reaction mixtures at temperatures from $-78°$ C. to $200°$ C. Each W is independently substituted with 0 to 3 $R^{29}$ groups. Typically, W is a saturated, unsaturated or aromatic ring comprising a mono- or bicyclic carbocycle or heterocycle. More typically, W has 3 to 10 ring atoms, still more typically, 3 to 7 ring atoms, and ordinarily 3 to 6 ring atoms. The W rings are saturated when containing 3 ring atoms, saturated or monounsaturated when containing 4 ring atoms, saturated, or mono- or diunsaturated when containing 5 ring atoms, and saturated, mono- or diunsaturated, or aromatic when containing 6 ring atoms.

When W is carbocyclic, it is typically a 3 to 7 carbon monocycle or a 7 to 12 carbon atom bicycle. More typically, W monocyclic carbocycles have 3 to 6 ring atoms, still more typically 5 or 6 ring atoms. W bicyclic carbocycles typically have 7 to 12 ring atoms arranged as a bicyclo [4,5], [5,5], [5,6] or [6,6] system, typically, 9 or 10 ring atoms arranged as a bicyclo [5,6] or [6,6] system. Examples include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

A W heterocycle is typically a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). More typically, W heterocyclic monocycles have 3 to 6 ring atoms (2 to 5 carbon atoms and 1 to 2 heteroatoms selected from N, O, and S), still more typically, 5 or 6 ring atoms (3 to 5 carbon atoms and 1 to 2 heteroatoms selected from N and S). W heterocyclic bicycles typically have 7 to 10 ring atoms (6 to 9 carbon atoms and 1 to 2 heteroatoms selected from N, O, and S)

arranged as a bicyclo [4,5], [5,5], [5,6], or [6,6] system, still more typically, 9 to 10 ring atoms (8 to 9 carbon atoms and 1 to 2 hetero atoms selected from N and S) arranged as a bicyclo [5,6] or [6,6] system.

"Heterocycle" as used herein includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960).

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Typically W heterocycles are selected from pyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, or pyrrolyl.

More typically, the heterocycle of W is bonded through a carbon atom or nitrogen atom thereof. Still more typically W heterocycles are bonded by a stable covalent bond through a carbon or nitrogen atom thereof. Stable covalent bonds are chemically stable structures as described above.

W optionally is selected from the group consisting of:

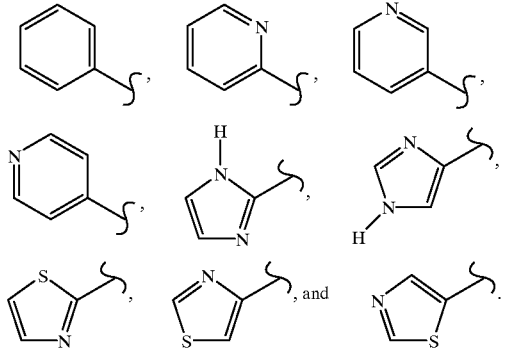

$R^5$ is H or $R^3$.

$R^7$ is H or an amino protecting group. $R^7$ amino protecting groups are described by Greene at pages 315–385. They include Carbamates (methyl and ethyl, 9-fluorenylmethyl, 9(2-sulfo)fluoroenylmethyl, 9-(2,7-dibromo) fluorenylmethyl, 2,7-di-t-buthyl-[9-(10,10-dioxo-10,10,10,10-tetrahydrothioxanthyl)]methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl) ethyl, 1-(3,5-di-t-butylphenyl)- 1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N-N Derivatives (N-nitro, N-nitroso, N-oxide); N-P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N-Si Derivatives; N-S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl). Typically, $R^7$ is H or a —C(O)$R^{25}$ ($R^{25}$ is described above).

$R^8$ is H or $R^2$. Typically $R^8$ is H.

$R^9$ is H or a thiol protecting group. $R^9$ amino protecting groups are described by Greene at pages 277–308. They include Thioethers (S-Benzyl, S-p-Methoxybenzyl, S-o- or p-Hydroxy- or Acetoxybenzyl, S-p-Nitrobenzyl, S-4-Picolyl, S-2-Picolyl N-Oxide, S-9-Anthrylmethyl, S-9-Fluorenylmethyl, S-Ferrocenylmethyl); S-Diphenylmethyl, Substituted S-Diphenylmethyl, and S-Triphenylmethyl Thioethers (S-Diphenylmethyl, S-Bis(4-methoxyphenyl) methyl, S-5-Dibenzosuberyl, S-Triphenylmethyl, S-Diphenyl-4-pyridylmethyl, S-Phenyl, S-2,4-Dinitrophenyl, S-t-Butyl, S-1-Adamantyl); Substituted S-Methyl Derivatives Monothio, Dithio, and Aminothio Acetals (S-Methoxymethyl, S-Isobutoxymethyl, S-2-Tetrahydropyranyl, S-Benzylthiomethyl, S-Phenylthiomethyl, Thiazolidines, S-Acetamidomethyl, S-Trimethylacetamidomethyl, S-Benzamidomethyl, S-Acetyl-, S-Carboxy-, and S-Cyanomethyl); Substituted S-Ethyl Derivatives (S-2-Nitro-1-phenylethyl, S-2-(4'-Pyridyl)ethyl, S-2-Cyanoethyl, S-2,2-Bis(carboethoxy) ethyl, S-1-m-Nitrophenyl-2-benzoylethyl, S-2-Phenylsulfonylethyl, S-1-(4-Methylphenylsulfonyl)-2-methylprop-2-yl); Silyl Thioethers, Thioesters, (S-Acetyl Derivative, S-Benzoyl Derivative, S-N-[[(p-Biphenylyl) isopropoxy]carbonyl]-N-methyl-γ-aminobutyrate, S-N-(t-Butoxycarbonyl)-N-methyl-γ-aminobutyrate); Thiocarbonate Derivatives (S-2,2,2-Trichloroethoxycarbonyl, S-t-Butoxycarbonyl, S-Benzyloxycarbonyl, S-p-Methoxybenzyloxycarbonyl); Thiocarbamate Derivatives (S-(N-Ethyl), S-(N-Methoxymethyl); Miscellaneous Derivatives, Unsymmetrical Disulfides (S-Ethyl, S-t-Butyl, Substituted S-Phenyl); Sulfenyl Derivatives (S-Sulfonate, S-Sulfenylthiocarbonate, S-3-Nitro-2-pyridinesulfenyl Sulfide); Protection for Dithiols, Dithio Acetals and Ketals (S,S'-Methylene, S,S'-Isopropylidene, and S,S'-Benzylidene, S,S'-p-Methoxybenzylidene); Protection for Sulfides (S-Methylsulfonium Salt, S-Benzyl- and S-4-Methoxybenzylsulfonium Salt, S-1-(4-Phthalimidobutyl) sulfonium Salt); S-P Derivatives (S-(Dimethylphosphino) thioyl, S-(Diphenylphosphino)thioyl);

Each $R^{21}$ is independently $R^{20}$, Br, Cl, F, I CN, NO$_2$ or N$_3$. Typically, $R^{21}$ is Cl, F or $R^{20}$, more typically, $R^{20}$, still more typically, H.

Each $R^{22}$ is independently F, Cl, Br, I, —CN, N$_3$, —NO$_2$, —OR$^5$, —OR$^{20}$, —N(R$^{20}$)$_2$, —N(R$^{20}$)(R$^7$), —N(R$^7$)$_2$, —SR$^{20}$, —SR$^9$, —S(O)R$^{20}$, —S(O)$_2$R$^{20}$, —S(O)OR$^{20}$, —S(O)OR$^8$, —S(O)$_2$OR$^{20}$, —S(O)$_2$OR$^8$, —C(O)OR$^{20}$, —C(O)OR$^8$, —OC(O)R$^{20}$, —N(R$^{20}$)(C(O)R$^{20}$), —N(R$^7$)(C(O)R$^{20}$), —N(R$^{20}$)(C(O)OR$^{20}$), —N(R$^7$)(C(O)OR$^{20}$), —C(O)N(R$^{20}$)$_2$, —C(O)N(R$^7$)(R$^{20}$), —C(O)N(R$^7$)$_2$, —C(NR$^{20}$)(N(R$^{20}$)$_2$), —C(N(R$^7$))(N(R$^{20}$)$_2$), —C(N(R$^{20}$))(N(R$^{20}$)(R$^7$)), —C(N(R$^7$))(N(R$^{20}$)(R$^7$)), —C(N(R$^{20}$))(N(R$^7$)$_2$), —C(N(R$^7$))(N(R$^7$)$_2$), —N(R$^{20}$)C(N(R$^{20}$))(N(R$^{20}$)$_2$), —N(R$^{20}$)C(N(R$^{20}$))(N(R$^{20}$)(R$^7$)), —N(R$^{20}$)C(N(R$^7$))(N(R$^{20}$)$_2$), —N(R$^7$)C(N(R$^{20}$))(N(R$^{20}$)$_2$), —N(R$^7$)C(N(R$^7$))(N(R$^{20}$)(R$^7$)), —N(R$^{20}$)C(N(R$^{20}$))(N(R$^{20}$)(R$^7$)), —N(R$^{20}$)C(N(R$^7$)(N(R$^{20}$)(R$^7$)), —N(R$^{20}$)C(N(R$^{20}$))(N(R$^7$)$_2$), —N(R$^7$)C(N(R$^7$))(N(R$^{20}$)(R$^7$)), —N(R$^7$)C(N(R$^{20}$))(N(R$^7$)$_2$), —N(R$^{20}$)C(N(R$^7$))(N(R$^7$)$_2$), —N(R$^7$)C(N(R$^7$))(N(R$^7$)$_2$), =O, =S, =N(R$^{20}$), =N(R$^7$) or W.

Typically $R^{22}$ is F, Cl, Br, I, —CN, N$_3$, —NO$_2$, —OR$^5$, —OR$^{20}$, —N(R$^{20}$)$_2$, —N(R$^{20}$)(R$^7$), —N(R$^7$)$_2$, —SR$^{20}$, —SR$^9$, —S(O)R$^{20}$, —S(O)$_2$R$^{20}$, —S(O)OR$^{20}$, —S(O)OR$^8$, —S(O)$_2$OR$^{20}$, —S(O)$_2$OR$^8$, —C(O)OR$^{20}$, —C(O)OR$^8$, =O, =S, =N(R$^{20}$) or =N(R$^7$). More typically $R^{22}$ is F, Cl, Br, —CN, N$_3$, —NO$_2$, —OR$^5$, —OR$^{20}$, —N(R$^{20}$)$_2$, —N(R$^{20}$)(R$^7$), —N(R$^7$)$_2$, —C(O)OR$^{20}$, —C(O)OR$^8$, or =O. Still more typically $R^{22}$ is F, Cl, Br, —CN, N$_3$, —NO$_2$, —OR$^{20}$, —N(R$^{20}$)$_2$, —C(O)OR$^{20}$ or =O. More typically yet $R^{22}$ is F, Cl, Br, —CN, —OH, —N(H)$_2$, —C(O)OR$^{20}$ or =O.

Each $R^{23}$ is independently alkyl of 1 to 11 carbon atoms, alkenyl of 2 to 11 carbon atoms, or alkynyl of 2 to 11 carbon atoms. More typically $R^{23}$ is alkyl of 1 to 8 carbon atoms, alkenyl of 2 to 8 carbon atoms, or alkynyl of 2 to 8 carbon atoms, still more typically, $R^{23}$ is alkyl of 1 to 6 carbon atoms, alkenyl of 2 to 6 carbon atoms, or alkynyl of 2 to 6 carbon atoms. More typically yet, $R^{23}$ is $R^{25}$.

Each $R^{24}$ is independently $R^{23}$ wherein each $R^{23}$ is substituted with 0 to 3 $R^{22}$ groups. Each of the typical embodiments of $R^{23}$ and $R^{22}$ are typical of $R^{24}$. More typically $R^{24}$ is substituted with 0, 1, 2, or 3 $R^{22}$ groups.

$R^{24a}$ is independently alkylene of 1 to 11 carbon atoms, alkenylene of 2 to 11 carbon atoms, or alkynylene of 2–11 carbon atoms any one of which alkylene, alkenylene or alkynylene is substituted with 0–3 $R^{22}$ groups; compound. More typically $R^{24a}$ is alkylene of 1 to 8 carbon atoms, alkenylene of 2 to 8 carbon atoms, or alkynylene of 2 to 8 carbon atoms, still more typically, $R^{24a}$ is alkylene of 1 to 6 carbon atoms, alkenylene of 2 to 6 carbon atoms, or alkynylene of 2 to 6 carbon atoms. More typically yet, $R^{24a}$ is —CH$_2$—, —CH$_2$CH$_2$—, —CH$_2$CH$_2$CH$_2$— or —C(H)(CH$_3$)—.

Each $R^{28}$ is independently alkyl of 1 to 12 carbon atoms, alkenyl of 2 to 12 carbon atoms, or alkynyl of 2 to 12 carbon atoms. More typically $R^{28}$ is alkyl of 1 to 8 carbon atoms, alkenyl of 2 to 8 carbon atoms, or alkynyl of 2 to 8 carbon atoms, still more typically, $R^{28}$ is alkyl of 1 to 6 carbon atoms, alkenyl of 2 to 6 carbon atoms, or alkynyl of 2 to 6 carbon atoms. More typically yet, $R^{28}$ is $R^{25}$.

Each $R^{29}$ is independently $R^{22}$ or $R^{28}$ wherein each $R^{28}$ is substituted with 0 to 3 $R^{22}$ groups. Each of the typical embodiments of $R^{28}$ and $R^{22}$ are typical of $R^{29}$. More typically $R^{29}$ is substituted with 0, 1, 2, or 3 $R^{22}$ groups.

Each $R^{30}$ is independently H, $R^{24}$, W or —$R^{24a}$W.

$R^4$ is —C($R^{30}$)$_3$, provided that $R^4$, taken as a whole, contains 0 to 1 W groups (W is described above) substituted with 0 to 3 $R^{29}$ groups ($R^{29}$ is described above); and, in addition, 1 to 12 carbon atoms substituted with 0 to 3 $R^{22}$ groups ($R^{22}$ is described above). Exemplary embodiments of $R^4$ are provided as $U_1$ embodiments in the documents cited in the "Brief Description of Related Art" above.

Typically one $R^{30}$ is H. More typically, one $R^{30}$ is H and the remaining two $R^{30}$'s are independently $R^{24}$, W or —$R^{24a}$W. More typically yet, one $R^{30}$ is H, one $R^{30}$ is $R^{24}$ and the remaining $R^{30}$ is independently $R^{24}$, W or —$R^{24a}$W.

In one embodiment of $R^4$, one $R^{30}$ is H, one $R^{30}$ is $R^{25}$ and one $R^{30}$ is $R^{24}$, W or —$R^{24a}$W. Typically, one $R^{30}$ is H and two $R^{30}$'s are $R^{25}$. In another embodiment of $R^4$, one $R^{30}$ is H, one $R^{30}$ is —$R^{24a}$W and one $R^{30}$ is $R^{24}$, W or —$R^{24a}$W. Typically, one $R^{30}$ is H, one $R^{30}$ is —$R^{24a}$W and one $R^{30}$ is $R^{24}$. In another embodiment, one $R^{30}$ is H and two $R^{30}$'s are alkyl of 1 to 6 carbon atoms.

In another embodiment, $R^4$ is:

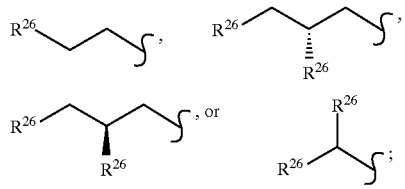

wherein $R^{26}$ is H, —CH$_3$, —CH$_2$CH$_3$, —CH$_2$CH$_2$CH$_3$, —OCH$_3$, —OAc (—O—C(O)CH$_3$), —OH, -NH$_2$, or —SH, typically H, —CH$_3$ or —CH$_2$CH$_3$.

Typically each $R^4$ (taken as a whole) contains 0–3 W groups each of which is independently substituted with 0–3 $R^{29}$ groups; and each $R^4$ (taken as a whole) in addition contains 1–12 carbon atoms, each carbon atom of which is independently substituted with 0–3 $R^{22}$ groups. More typically each $R^4$ contains 0, 1 or 2 such W groups, more typically yet, 0 or 1 such W group.

In another embodiment, each $R^{30}$ group (taken as whole) of $R^4$ is not so electron withdrawing as to prevent the formation of compound 11. Lowry, T. H. and Richardson, K. S. "Mechanism and Theory in Organic Chemistry" (Harper & Row, 1976) at section 2.2, pages 60–71, and March, J. "Advanced Organic Chemistry" (McGraw-Hill, 1977) at Chapter 9, Quantitative Treatments of the Effect of Structure on Reactivity", pages 251–259, provide details of the electron withdrawing properties of substitutent groups. In another embodiment, each $R^{30}$ group (taken as whole) of $R^4$ has a Hammett $\sigma_{para}$ value of less than about 1, typically less than about 0.75, more typically less than about 0.5. In another embodiment, each $R^{30}$ group (taken as whole) of $R^4$ has a Hammett $\sigma_{para}$ value of −1.0 to 1.0, more typically −0.75 to 0.75, more typically yet −0.5 to 0.5.

This process embodiment comprises reaction of a compound of the formula:

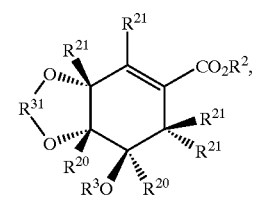

10 wherein $R^{31}$ is a ketal or acetal, with a lewis acid reagent. Typically $R^{31}$ is —C($R^{30}$)$_2$— wherein $R^{30}$ is as described above.

Typically, compound 10 is reacted with a Lewis acid catalyst common in the art, such as BF$_3$•Et$_2$O, TiCl$_3$, TMSOTf, SmI$_2$(THF)$_2$, LiClO$_4$, Mg(ClO$_4$)$_2$, Ln(OTf)$_3$ (where Ln=Yb, Gd, Nd), Ti(Oi-Pr)$_4$, AlCl$_3$, AlBr$_3$, BeCl$_2$, CdCl$_2$, ZnCl$_2$, BF$_3$, BCl$_3$, BBr$_3$, GaCl$_3$, GaBr$_3$, TiCl$_4$, TiBr$_4$, ZrCl$_4$, SnCl$_4$, SnBr4, SbCl$_5$, SbCl$_3$, BiCl$_3$, FeCl$_3$, UCl$_4$, ScCl$_3$, YCl$_3$, LaCl$_3$, CeCl$_3$, PrCl$_3$, NdCl$_3$, SmCl$_3$, EuCl$_3$, GdCl$_3$, TbCl$_3$, LuCl$_3$, DyCl$_3$, HoCl$_3$, ErCl$_3$, TmCl$_3$, YbCl$_3$, ZnI$_2$, Al(OPr$^i$)$_3$, Al(acac)$_3$, ZnBr$_2$, or SnCl$_4$. Optionally, compound 10 is also treated with a reducing reagent. Typical reducing reagents are of the form B($R^{30}$)$_3$ such as BH$_3$. Optionally reducing reagents of the form B($R^{30}$)$_3$ are complexed with common solvents such as diethylether and dimethylsulfide. A wide range of borane reducing reagents are known and will not be described in detail here. For example Brown, H. C. "Boranes in Organic Chemistry", (Cornell Univ. Press, Ithaca, N.Y., 1972) (Brown) provides a very large number of examples such as is found in Part Four, Selective Reductions, pages 209–251, Part Five, Hydroboration, pages 255–297, and Part Six, Organoboranes, pages 301–446.

In a typical embodiment, compound 10 is treated with a lewis acid in a nonprotic solvent. More typically, compound 10 is treated with a lewis acid and a reducing reagent in a nonprotic solvent.

In a typical embodiment, a solution of 10 in dichlorormethane is cooled and treated with borane-methyl sulfide complex and trimethylsilyl trifluoromethanesulfonate. 10% Aqueous sodium bicarbonate solution is slowly added. The mixture is warmed to ambient temperature and stirred. The organic layer is filtered and concentrated in vacuo to leave compound 11. A detailed example of this embodiment is provided as Example 6 below.

In another example process of this embodiment compound 11 is of the formula:

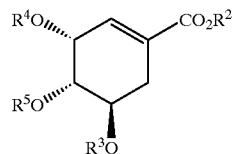

12

Another aspect of the present invention is directed to processes for the preparation of compounds of the formula:

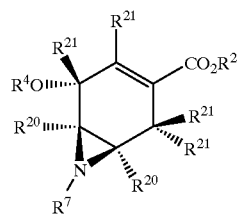

31 wherein:

$R^2$, $R^4$, $R^7$, $R^{20}$ and $R^{21}$ are as defined above.

This process embodiment comprises reaction of a compound of the formula:

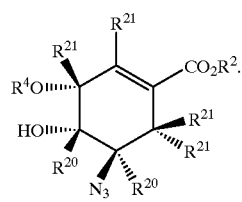

30 with a reducing reagent.

The azide of compound 30 is reduced to form compound 31.

Typically the process comprises treating compound 30 with a reducing agent to form compound 31. More typically the process comprises treating compound 30 with hydrogen gas and a catalyst (such as platinum on carbon or Lindlar's catalyst), or reducing reagents (typically a trisubstituted phosphine such as trialkyl ($P(R^{25})_3$) or triaryl phosphine ($PW_3$, e.g. triphenylphosphine). More typically still, the process comprises treating compound 30 with triphenylphosphine and a base to form compound 31.

Typically, compound 30 is disolved in a suitable polar, aprotic solvent such as anhydrous acetonitrile. A solution of anhydrous triphenylphosphine in a suitable solvent such as anhydrous tetrahydrofuran or a mixture of solvents is added dropwise. The mixture is heated at reflux then concentrated in vacuo to leave compound 5. A detailed example of this embodiment is provided as Example 9 below.

In another embodiment of this process compound 31 is of the formula:

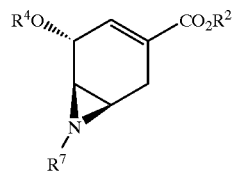

32

Another aspect of the present invention is directed to processes for the preparation of compounds of the formula:

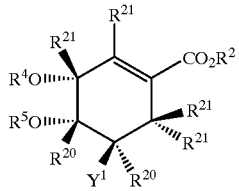

41 wherein:

$R^2$, $R^4$, $R^5$, $R^{20}$ and $R^{21}$ are as described above.

$Y^1$ is a mono-, di- or unsubstituted amino group. Typically $Y^1$ is of the formula —$N(R^{30})_2$, a phthalimide or is a nitrogen containing heterocycle (defined above under W), more typically, $Y^1$ is a phthalimide, more typically yet, a phthalimide salt.

This process embodiment comprises reaction of a compound of the formula:

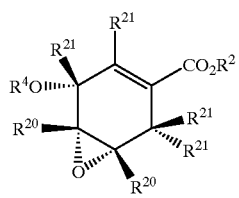

40 with an amine reagent. Typically, the amine reagent is of the formula $HY^1$ or a salt of $HY^1$, such as, by way of example, $NH_3$ (McManns, et al., "Bull Soc. Chim. France" 850 (1947)), $HY^1$ generally (Moussevon, M., et al., "Synth. Commun." 3:177 (1973)) or phthalimide (Gabriel, et al., "Ber." 20:2224 (1887) or Gibson, et al., "Angew. Chem. Int.", 7:919–930 (1968)).

The process comprises treating compound 40 with the amine reagent to produce compound 32. More typically, compound 40 is treated with the amine reagent in a suitable polar a protic solvent (e.g. $CH_3CN$, DMF or THF). Optionally compound 40 is treated with the amine reagent and a base. Typical details of this process embodiment can be found in March, "Advanced Organic Chemistry" 4th. ed., pp 425–427.

In another embodiment of this process compound 41 is of the formula:

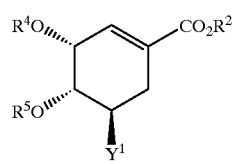

42

Another aspect of the present invention is directed to processes for the preparation of compounds of the formula:

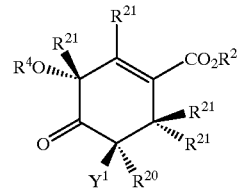

51 wherein:

$R^2$, $R^4$, $R^{20}$, $R^{21}$ and $Y^1$ are as described above;

This process embodiment comprises reaction of a compound of the formula:

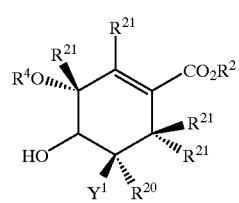

50 with an oxidizing reagent. A wide range of suitable oxidation reagents are common in the art and will not be detailed here. For example House, H.O. "Modern Synthetic Reactions, Second Edition", Chapter 5, pages 259–273, describes the selective oxidation of alcohols. Typical reagents include $CrO_3$, $Na_2Cr_2O_7$, $KMnO_4$, PDC and PCC. Typical details of this process embodiment can be found in Larock, "Comprehensive Organic Transformations", pp. 604–614; Corey et al., "Tetrahedron Lett." 31:2647–50 (1975); Ley et al., "Chem. Common" 1625 (1987); Sweon, et al., "J. Org. Chem." 43:2480–2 (1978); and Martin, et al., "J. Org. Chem." 48:4155–56 (1983). Solvents typically include inert polar solvents (e.g. $CH_2Cl_2$, toluene or $CH_3CN$).

In another embodiment of this process compound 51 is of the formula:

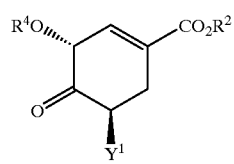

52

Another aspect of the present invention is directed to processes for the preparation of compounds of the formula:

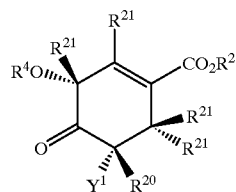

61 wherein:

$R^2$, $R^4$, $R^{20}$, $R^{21}$ and $Y^1$ are as described above;

This process embodiment comprises reaction of a compound of the formula:

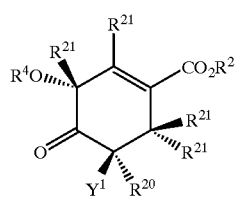

51 with a base. Typically the base is a hindered amine or hindered alkoxide or the salts of either. More typically the base is of the formula $NaOR^{25}$, $KOR^{25}$ or $NR^{25}{}_3$, more typically yet, DBN, DBU or diisopropyl ethyl amine.

In another embodiment of this process compound 61 is of the formula:

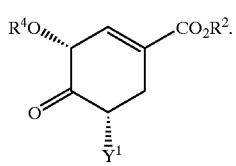

62

Another aspect of the present invention is directed to processes for the preparation of compounds of the formula:

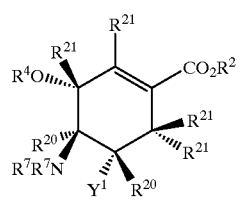

71 wherein:

$R^2$, $R^4$, $R^7$, $R^{20}$, $R^{21}$ and $Y^1$ are as described above;

This process embodiment comprises reaction of a compound of the formula:

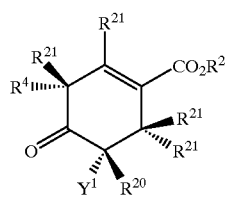

with a reductive amination reagent. Typical details of and references to this process embodiment can be found in Larock, op. cit., pp. 421–425. Another typical description (NaCNBH$_3$ method) is Borch, "J. Am. Chem. Soc." 93:2897–2904 (1971).

Schemes 1 and 2 depict embodiments of the invention. Detailed descriptions of the processes of Schemes 1 and 2 are provided in the Examples (below).

Additional individual process embodiments of the invention include any one or sequential combination of processes AA, AB, AC, AD, AE, AF, AG, AH, AI, AJ, or AK of Schemes 1 and 2. "Sequential combination" as used herein means more than one process wherein the individual processes are performed one after the other in the order shown. Isolation, separation, purification is optionally performed prior to any of the individual processes.

Additional individual process embodiments of the invention include any one or sequential combination of the processes of Example 1, Example 2, Example 3, Example 4, Example 5, Example 6, Example 7, Example 8, Example 9, Example 10, Example 11, Example 12 or Example 13.

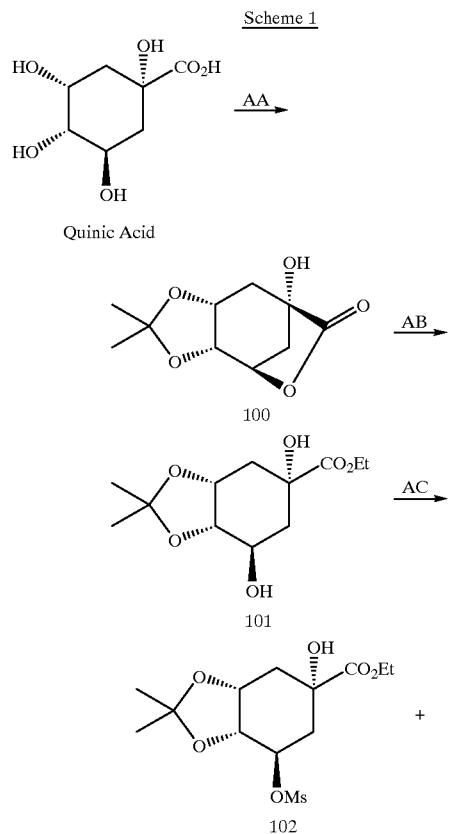

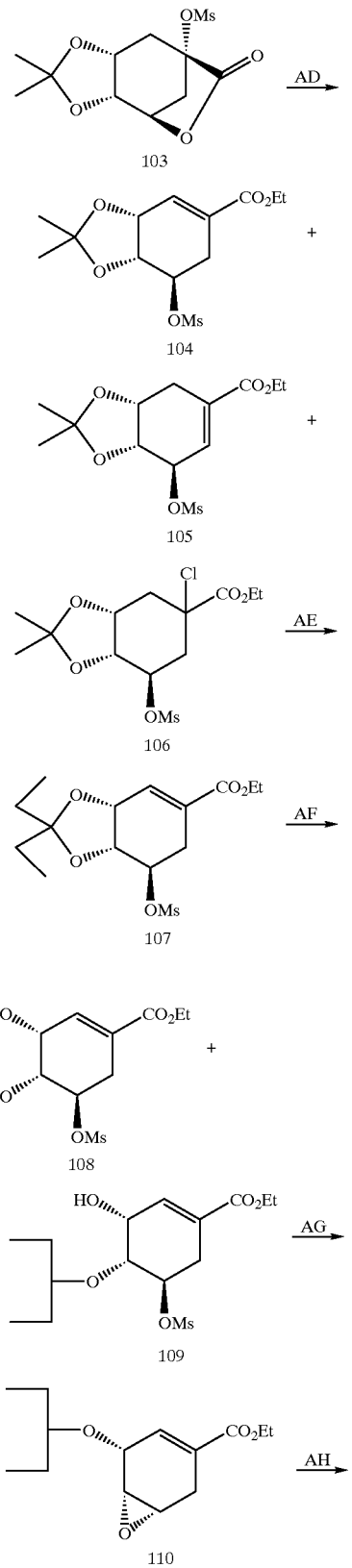

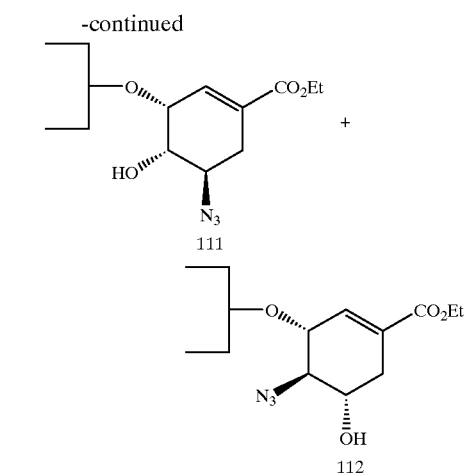

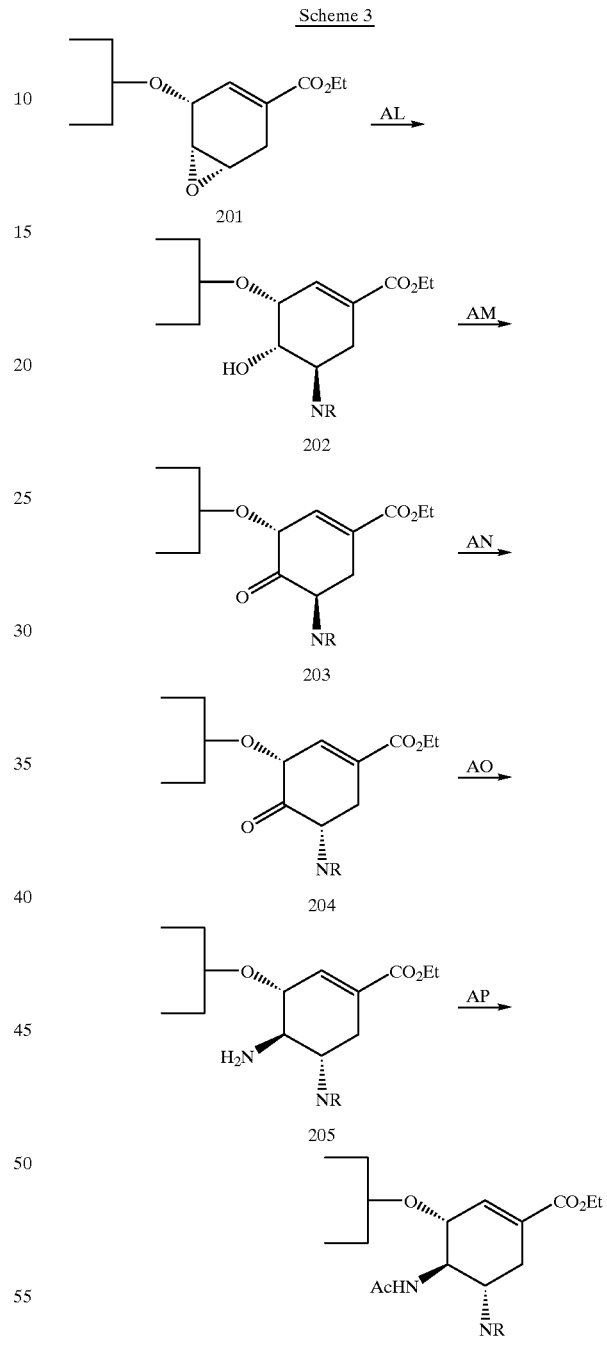

Scheme 3 depicts the synthesis of the neuraminidase inhibitor 206 (R=H$_2$) by use of alternative nitrogen nucleophiles (March, "Advanced Organic Chemistry" 4th. ed., pp 425–427) to open the epoxide 201. Oxidation of azidoalcohol 202 gives ketone 203 (Larock, "Comprehensive Organic Transformations", pp. 604–614) in which the β-axial NR group isomerizes to the α-equatorial configuration 204. Reductive amination of the ketone 204 (Larock, op. cit., pp. 421–425) gives the β-equatorial amine 205 which is acetylated to afford 206. Cleavage of the R moiety (Greene, "Protective Groups in Organic Synthesis", pp. 218–287) gives the neuramidase inhibitor 206 (R=H$_2$).

Additional individual process embodiments of the invention include any one or sequential combination of processes AL, AM, AN, AO, or AP of Scheme 3.

Modifications of each of the above schemes leads to various analogs of the specific exemplary materials produced above. The above cited citations describing suitable methods of organic synthesis are applicable to such modifications.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Stereoisomers

The compounds of the invention are enriched or resolved optical isomers at any or all asymmetric atoms. For example, the chiral centers apparent from the depictions are provided as the chiral isomers or racemic mixtures. Both racemic and diasteromeric mixtures, as well as the individual optical isomers isolated or synthesized, substantially free of their enantiomeric or diastereomeric partners, are all within the scope of the invention.

One or more of the following enumerated methods are used to prepare the enantiomerically enriched or pure isomers herein. The methods are listed in approximately their order of preference, i.e., one ordinarily should employ stereospecific synthesis from chiral precursors before chromatographic resolution before spontaneous crystallization.

Stereospecific synthesis is described in the examples. Methods of this type conveniently are used when the appropriate chiral starting material is available and reaction steps are chosen do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis. If an unexpected racemization occurs in a method thought to be stereospecific then one needs only to use one of the following separation methods to obtain the desired product.

If a suitable stereospecific synthesis cannot be empirically designed or determined with routine experimentation then those skilled in the art would turn to other methods. One method of general utility is chromotographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3–4, 1987. Examples of chiral columns that could be used to screen for the optimal separation technique would include Diacel Chriacel OD, Regis Pirkle Covalent Dphenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desireable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separting the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of embodiments of this invention and then separated by chromatography.

Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enatiomeric mixture separates from solution or a melt as a conglomerate, i.e., a mixture of enantiomerically-pure crystals, then the crystals can be mechanically separated, thereby producing the enantiomerically enriched preparation. This method, however, is not practical for large scale preparations and is of no value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4). In particular, Part 2, "Resolution of Enantiomer Mixture", pages 217–435; more particularly, section 4, "Resolution by Direct Crystallization", pages 217–251, section 5, "Formation and Separation of Diastereomers", pages 251–369, section 6, "Crystallization-Induced Asymmetric Transformations", pages 369–378, and section 7, "Experimental Aspects and Art of Resolutions", pages 378–435; still more particularly, section 5.1.4, "Resolution of Alcohols, Transformation of Alcohols into Salt-Forming Derivatives", pages 263–266, section 5.2.3, "Covalent Derivatives of Alcohols, Thiols, and Phenols", pages 332–335, section 5.1.1, "Resolution of Acids", pages 257–259, section 5.1.2, "Resolution of Bases", pages 259–260, section 5.1.3, "Resolution of Amino Acids", page 261–263, section 5.2.1, "Covalent Derivatives of Acids", page 329, section 5.2.2, "Covalent Derivatives of Amines", pages 330–331, section 5.2.4, "Covalent Derivatives of Aldehydes, Ketones, and Sulfoxides", pages 335–339, and section 5.2.7, "Chromatographic Behavior of Covalent Diastereomers", pages 348–354, are cited as examples of the skill of the art.

Salts and Hydrates

The compositions of this invention optionally comprise salts of the compounds herein, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds of the invention in their un-ionized, as well as zwitterionic form, and combinations with stoichimetric amounts of water as in hydrates.

Also included within the scope of this invention are the salts of the parental compounds with one or more amino acids. Any of the amino acids described above are suitable, especially the naturally-occuring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Additional Uses for the Compounds of This Invention

The compounds of the invention are polyfunctional. As such they represent a unique class of monomers for the synthesis of polymers. By way of example and not limitation, the polymers prepared from the compounds of this invention include polyamides, polyesters and mixed polyester-polyamides.

The present compounds are used as monomers to provide access to polymers having unique pendent functionalities. The compounds of this invention are useful as comonomers with monomers which do not fall within the scope of the invention. Polymers of the compounds of this invention will have utility as cation exchange agents (polyesters or polyamides) in the preparation of molecular sieves (polyamides), textiles, fibers, films, formed articles and the like. Polymers are prepared by any conventional method, for example, by cross-linking an —OH or —$NH_2$ group of the compounds of the invention with a diacid comonomer. The preparation of these polymers from the compounds of the invention is conventional per se.

The compounds of the invention are also useful as a unique class of polyfunctional surfactants. Particularly when $R^4$ or $R^2$ do not contain hydrophilic substituents and are, for example, alkyl, the compounds have the properties of bi-functional surfactants. As such they have useful surfactant, surface coating, emulsion modifying, rheology modifying and surface wetting properties.

As polyfunctional compounds with defined geometry and carrying simultaneously polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters or amides with a compound of the invention containing an —OH or —$NH_2$ group; 2) separating the diastereomers; and 3) hydrolyzing the ester structure. Further, such a method can be used to resolve the compounds of the invention themselves if optically active acids are used instead of racemic starting materials.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups in the compounds of this invention are suitable for use in cross-linking. For example, —OH and —$NH_2$ groups. Suitable protection of reactive groups will be used where necessary while assembling the cross-linked reagent to prevent polymerization of the bifunctional compound of this invention. In general, the compounds here are used by linking them through hydroxyl or amino groups to carboxylic or phosphonic acid groups of the first linked partner, then covalently bonding to the other binding partner through another —OH or —$NH_2$ group. For example a first binding partner such as a steroid hormone is reacted to form an amide bond with the —$NH_2$ group of a compound of this invention and then this conjugate is cross-linked through a hydroxyl to cyanogen bromide activated Sepaharose, whereby immobilized steroid is obtained. Other chemistries for conjugation are well known. See for example Maggio, "Enzyme-Immunoassay" (CRC, 1988, pp 71–135) and references cited therein.

The following examples are put forth so as to provide those of ordinary skill in the art with a complete disclosure and description of how to make the compounds and compositions of the invention and are not intended to limit the scope of what the inventors regard as their invention. Efforts have been made to insure accuracy with respect to numbers used (e.g., amounts, temperatures, etc.), but some experimental errors and deviations should be taken into account. Unless indicated otherwise, parts are parts by weight, temperature is in degrees Centigrade, and pressure is at or near atmospheric.

EXAMPLES

Example 1

Lactone 100: A solution of quinic acid (20 kg, 104 mol; $[\alpha]_D$ –43.7° (c=1.12, water); "Merck Index 11th ed", 8071: $[\alpha]_D$ –42° to –44° (water)), 2,2-dimethoxypropane (38.0 kg, 365 mol) and p-toluenesulfonic acid monohydrate (0.200 kg, 1.05 mol) in acetone (80 kg) was heated at reflux for two hours. The reaction was quenched by addition of 21% sodium ethoxide in ethanol (0.340 kg, 1.05 mol) and most of the solvent was distilled in vacuo. The residue was partitioned between ethyl acetate (108 kg) and water (30 kg). The aqueous layer was back-extracted with ethyl acetate (13 kg) and the combined organic layers were washed with 5% aqueous sodium bicarbonate (14 kg). Most of the ethyl acetate was distilled in vacuo to leave a pale yellow solid residue of 100 which was used directly in the next step.

Example 2

Hydroxy ester 101: A solution of the crude lactone 100 (from 104 mol (–)-quinic acid) in absolute ethanol (70 kg) was treated with 20% sodium ethoxide in ethanol (0.340 kg, 1.05 mol). After two hours at room temperature, acetic acid (0.072 kg, 1.2 mol) was added and the solvent was distilled in vacuo. Ethyl acetate (36 kg) was added and the distillation continued to near dryness. The tan solid residue composed of a ca. 5:1 mixture of 101:100 was dissolved in ethyl acetate (9 kg) at reflux and hexane (9 kg) was added. Upon cooling, a white crystalline solid formed which was isolated by filtration to afford a ca. 6.5:1 mixture of 101:100 (19.0 kg, 70% yield).

Example 3

Mesyl ester 102: A solution of a ca. 6.5:1 mixture (18.7 kg, ca. 72 mol) of hydroxy ester 101 and lactone 100 in dichloromethane (77 kg) was cooled to 0–10° C. and treated with methanesulfonyl chloride (8.23 kg, 71.8 mol), followed by slow addition of triethylamine (10.1 kg, 100 mol). An additional portion of methanesulfonyl chloride (0.84 kg, 7.3 mol) was added. After one hour, water (10 kg) and 3% hydrochloric acid (11 kg) were added. The layers were separated and the organic layer was washed with water (9 kg), then distilled in vacuo to leave a semi-solid residue composed of a ca. 6.5:1 mixture of mesyl ester 102 and mesyl lactone 103. The residue was dissolved in ethyl acetate (11 kg) and cooled to –10° to –20° C. for two hours. Mesyl lactone 103 crystallized and was separated by filtration and washed with cold ethyl acetae (11 kg). The filtrate was concentrated to afford mesyl ester 102 as an orange resin (20.5 kg, 84.3% yield).

Example 4

Mesyl acetonide 104: A solution of mesyl ester 102 (10.3 kg, 30.4 mol) and pyridine (10.4 kg, 183 mol) in dichloromethane (63 kg) was cooled to –20° to –30° C. and treated portionwise with sulfuryl chloride (6.22 kg, 46 mol). After the exothermic reaction subsided, the resulting slurry was quenched with ethanol (2.4 kg), warmed to 0° C., and washed successively with 16% sulfuric acid (35 kg), water (15 kg) and 5% aqueous sodium bicarbonate (1 kg). The organic layer containing a ca. 4:1:1 mixture of 104:105:106 was concentrated in vacuo and ethyl acetate (14 kg) was added. The allylic mesylate 105 was selectively removed by treatment of the ethyl acetate solution with pyrrolidine (2.27 kg, 31.9 mol) and tetrakis(triphenylphosphine)palladium(0) (0.0704 kg, 0.061mol) at ambient temperature for five hours, followed by washing with 16% sulfuric acid (48 kg). The organic layer was filtered through a pad of silica gel (11 kg) and eluted with ethyl acetate (42 kg). The filtrate was concentrated in vacuo to leave a thick orange oil composed of a ca. 4:1 mixture of 104:106. The residue was dissolved in ethyl acetate (5.3 kg) at reflux and hexane (5.3 kg) was added. Upon cooling, mesyl acetonide 104 crystallized and was separated by filtration and washed with 14% ethyl acetate in hexane (2.1 kg). After drying in vacuo, 104 was obtained as pale yellow needles (4.28 kg, 43.4% yield), mp 102–3° C.

Example 5

Pentyl ketal 107: A solution of acetonide 104 (8.9 kg, 27.8 mol), 3-pentanone (24 kg, 279 mol) and 70% perchloric acid (0.056 kg, 0.39 mol) was stirred for 18 hours. The volatiles were distilled in vacuo at ambient temperature and fresh 3-pentanone (30 kg, 348 mol) was added gradually as the distillation progressed. The reaction mixture was filtered, toluene (18 kg) was added, and the resulting solution was washed successively with 6% aqueous sodium bicarbonate (19 kg), water (18 kg) and brine (24 kg). The organic layer was concentrated in vacuo and toluene (28 kg) was added gradually as the distillation progressed. When no more distilled, the residual orange oil was composed of pentyl ketal 107 (9.7 kg, 100% yield) and toluene (ca. 2 kg).

Example 6

Pentyl ether 108: A solution of ketal 107 (8.6 kg, 25 mol) in dichloromethane (90 kg) was cooled to –30° to –20° C. and treated with borane-methyl sulfide complex (2.1 kg, 27.5 mol) and trimethylsilyl trifluoromethanesulfonate (7.2 kg, 32.5 mol). After one hour, 10% aqueous sodium bicarbonate solution (40 kg) was slowly added. The mixture was warmed to ambient temperature and stirred for 12 hours. The organic layer was filtered and concentrated in vacuo to leave a ca. 8:1 mixture of 108:109 as a gray waxy solid (7.8 kg, 90% yield).

Example 7

Epoxide 110: A ca. 8:1 mixture of isomeric pentyl ethers 108:109 (7.8 kg, 22.3 mol) in ethanol (26 kg) was treated with a solution of potassium hydrogen carbonate (3.52 kg, 35 mol) in water (22 kg). After heating at 55°–65° C. for two hours, the solution was cooled and twice extracted with hexanes (31 kg, then 22 kg). Unreacted 109 remained in the aqueous ethanol layer. The combined hexane extracts were filtered and concentrated in vacuo to leave epoxide 110 as a flocculent white crystalline solid (3.8 kg, 60% yield), mp=54.6° C.

Example 8

Hydroxy azide 111: A mixture of epoxide 110 (548 g, 2.0 mol), sodium azide (156 g, 2.4 mol) and ammonium chloride (128.4 g, 2.4 mol) in water (0.265 L) and ethanol (1.065 L) was heated at 70°–75° C. for eight hours. Aqueous sodium bicarbonate (0.42 L of 8% solution) was added and the ethanol was distilled in vacuo. The aqueous residue was extracted with ethyl acetate (1 L) and the extract was washed with water (0.5 L). The water wash was back-extracted with ethyl acetate (0.5 L). The combined organic extracts were washed with brine (0.5 L), dried over anhydrous sodium sulfate, filtered and concentrated in vacuo to leave a ca. 10:1 mixture of isomeric hydroxy azides 111:112 (608 g, 102% yield) as a dark brown oil.

Example 9

Aziridine 113: A ca. 10:1 mixture of hydroxy azides 111:112 (608 g, 2.0 mol) was three times co-evaporated in vacuo from anhydrous acetonitrile (3×0.3 L) and then dissolved in anhydrous acetonitrile (1 L). A solution of anhydrous triphenylphosphine (483 g, 1.84 mol) in anhydrous tetrahydrofuran (0.1 L) and anhydrous acetonitrile (0.92 L) was added dropwise over two hours. The mixture was heated at reflux for six hours then concentrated in vacuo to leave a golden paste composed of aziridine 113, triphenylphosphine oxide and traces of triphenylphosphine. The paste was triturated with diethyl ether (0.35 L). Most of the insoluble triphenylphosphine oxide was removed by filtration and washed with diethyl ether (1.5 L). The filtrate was concentrated in vacuo to leave a dark brown oil which was dissolved in 20% aqueous methanol and extracted three times with hexanes (3×1 L) to remove triphenylphosphine. The hexane extracts were back-extracted with 20% aqueous methanol (0.5 L) and the combined aqueous methanol layers were concentrated in vacuo. The residue was twice co-evaporated in vacuo from anhydrous acetonitrile (2×0.5 L) to leave a dark brown oil composed of aziridene 113 (490 g, 96.8 % yield) and triphenylphosphine oxide (ca. 108 g) which was used directly in the next step.

Example 10

Acetamido azide 115: A mixture of aziridine 113 (490 g, 1.93 mol) and triphenylphosphine oxide (ca. 108 g), sodium azide (151 g, 2.33 mol) and ammonium chloride (125 g, 2.33 mol) in dimethylformamide (1.3 L) was heated at 80°–85° C. for five hours. Sodium bicarbonate (32.8 g, 0.39 mol) and water (0.66 L) were added. The amino azide 114 was isolated from the reaction mixture by six extractions with hexanes (6×1 L). The combined hexane extracts were concentrated in vacuo to ca. 4.5 L total volume and dichloromethane (1.04 L) was added. Aqueous sodium bicarbonate (4.2 L of 8% solution, 3.88 mol) was added, followed by acetic anhydride (198 g, 1.94 mol). After stirring for one hour at ambient temperature, the aqueous layer was discarded. The organic phases were concentrated in vacuo to 1.74 kg total weight and dissolved with ethyl acetate (0.209 L) at reflux. Upon cooling, acetamido azide 115 crystallized and was isolated by filtration. After washing with cold 15% ethyl acetate in hexane (1 L) and drying in vacuo at ambient temperature, pure 115 was obtained as off-white crystals (361 g, 55% yield), mp 126–132° C.

Example 11

Acetamido amine 116: A mixture of azide 115 (549 g, 1.62 mol) and Lindlar catalyst (50 g) in abs. ethanol (3.25 L) was stirred for eighteen hours while hydrogen (1 atm.) was bubbled through the mixture. Filtration through Celite and concentration of the filtratein vacuo afforded 116 as a foam which solidified on standing (496 g, 98% yield).

Example 12

Phosphate salt of 116: A solution of acetamido amine 116 (5.02 g, 16.1 mmol) in acetone (75 mL) at reflux was treated with 85% phosphoric acid (1.85 g, 16.1 mmol) in abs. ethanol (25 mL). Crystallization commenced immediately and after cooling to 0° C. for 12 hours the precipitate was collected by filtration to affordd 116•$H_3PO_4$ as long colorless needles (4.94 g, 75% yield; $[\alpha]_D$ –39.9° (c=2 , water)), mp 203–4° C.

Example 13

Hydrochloride salt of 116: A solution of acetamido amine 116 (2.8 g, 8.96 mmol) in abs. ethanol (9 mL) was treated with 2.08 M hydrogen chloride in ethanol (8.6 mL, 17.9 mmol). Most of the ethanol was evaporated in vacuo and the oily residue was stirred with ethyl acetate (20 mL) until solid formed. Hexanes (20 mL) were gradually added to the stirred mixture. After one hour at ambient temperature, the solid was collected by filtration, washed with diethyl ether and dried in vacuo. This afforded 116•HCl as an off-white solid (2.54 g, 81% yield; $[\alpha]_D$ –43° (c=0.4, water)), mp206° C.

All literature and patent citations above are hereby expressly incorporated by reference in their entirety at the locations of their citation. Specifically cited sections or pages of the above cited works are incorporated by reference with specificity.

Whenever a compound described herein is substituted with more than one of the same designated group, such as, by was of example and not limitation, "$R^7$", "$R^8$", "$R^9$", "$R^{20}$" or "$R^{22}$", then it will be understood that each of the groups may be the same or different, i.e., each group is independently selected. So for example, the phrase "$R^{22}$ is" is synonymous with the phrase "each $R^{22}$ is independently".

The invention has been described in detail sufficient to allow one of ordinary skill in the art to make and use the subject matter of the following claims. It is apparent that certain modifications of the methods and compositions of the following claims can be made within the scope and spirit of the invention.

What is claimed is:

1. A process for preparation of compounds of the formula:

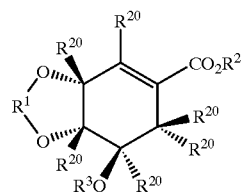

5 wherein:

$R^1$ is a cyclic hydroxy protecting group;

$R^2$ is a carboxylic acid protecting group;

$R^3$ is a hydroxy protecting group; and each $R^{20}$ is independently H or an alkyl of 1 to 12 carbon atoms;

which process comprises reaction of a compound of the formula:

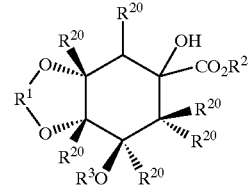

4 with a dehydrating reagent and separating compound 5 by treatment with a noble metal complex.

* * * * *